(12) United States Patent
Säll

(10) Patent No.: US 11,986,589 B2
(45) Date of Patent: May 21, 2024

(54) DOSE COUNTING MECHANISM FOR AN AEROSOL DISPENSER

(71) Applicant: SHL MEDICAL AG, Zug (CH)

(72) Inventor: Daniel Säll, Segeltorp (SE)

(73) Assignee: SHL MEDICAL AG, Zug (CH)

( * ) Notice: Subject to any disclaimer, the term of this patent is extended or adjusted under 35 U.S.C. 154(b) by 660 days.

(21) Appl. No.: 17/275,612

(22) PCT Filed: Sep. 12, 2019

(86) PCT No.: PCT/EP2019/074314
§ 371 (c)(1),
(2) Date: Mar. 11, 2021

(87) PCT Pub. No.: WO2020/064342
PCT Pub. Date: Apr. 2, 2020

(65) Prior Publication Data
US 2022/0031974 A1     Feb. 3, 2022

(30) Foreign Application Priority Data

Sep. 27, 2018 (EP) .................................... 18197311

(51) Int. Cl.
*A61M 15/00* (2006.01)
(52) U.S. Cl.
CPC .... *A61M 15/0073* (2014.02); *A61M 15/0081* (2014.02)
(58) Field of Classification Search
CPC .............. A61M 15/00; A61M 15/0001; A61M 15/0065; A61M 15/0068; A61M 15/007;
(Continued)

(56) References Cited

U.S. PATENT DOCUMENTS

| 5,988,496 A | 11/1999 | Bruna |
| 7,396,341 B2 | 7/2008 | Schyra et al. |

(Continued)

FOREIGN PATENT DOCUMENTS

| EP | 1065477 A2 | 1/2001 |
| JP | 2000503113 A | 3/2000 |

(Continued)

OTHER PUBLICATIONS

International Search Report and Written Opinion for Int. App. No. PCT/EP2019/074314, mailed Nov. 12, 2019.

*Primary Examiner* — Michael R Reid
*Assistant Examiner* — Sarah B Lederer
(74) *Attorney, Agent, or Firm* — McDonnell Boehnen Hulbert & Berghoff LLP

(57) ABSTRACT

A dose counting mechanism for an aerosol dispenser is presented where the dose counting mechanism has a first body structure, a second body structure rotatably attached to the first body structure, an annular dose counter provided with a plurality of teeth along its perimeter, the dose counter being arranged coaxially with the first body structure and the second body structure, each of the first body structure and the second body structure being rotatable relative to the dose counter, a rotatable actuator that meshes with the teeth of the dose counter, the actuator being configured to follow the perimeter of the dose counter when the second body structure is rotated relative to the first body structure, and a rotator that rotates concurrently with one of the first body structure and the second body structure and that engages with the actuator when rotation of the first body structure relative to the second body structure is initiated.

17 Claims, 8 Drawing Sheets

(58) Field of Classification Search
CPC ........ A61M 15/00071; A61M 15/0073; A61M 15/0081
See application file for complete search history.

(56) References Cited

U.S. PATENT DOCUMENTS

| | | | |
|---|---|---|---|
| 8,082,873 B2* | 12/2011 | Nuttall | A61M 15/009 116/285 |
| 8,291,898 B2* | 10/2012 | Southby | A61M 15/009 128/200.14 |
| 2004/0211420 A1 | 10/2004 | Minshull et al. | |
| 2010/0229855 A1 | 9/2010 | Howgill | |
| 2017/0361036 A1 | 12/2017 | Wang et al. | |

FOREIGN PATENT DOCUMENTS

| | | | |
|---|---|---|---|
| KR | 1999-0072148 A | 9/1999 | |
| WO | 96/16687 A1 | 6/1996 | |
| WO | 97/24586 A1 | 7/1997 | |

* cited by examiner

DOSE COUNTING MECHANISM FOR AN AEROSOL DISPENSER

CROSS REFERENCE TO RELATED APPLICATIONS

The present application is a U.S. National Phase Application pursuant to 35 U.S.C. § 371 of International Application No. PCT/EP2019/074314 filed Sep. 12, 2019, which claims priority to European Patent Application No. 18197311.6 filed Sep. 27, 2018. The entire disclosure contents of these applications are herewith incorporated by reference into the present application.

TECHNICAL FIELD

The present disclosure generally relates to aerosol dispensers.

BACKGROUND

Aerosol dispensers may be configured to provide multiple doses of a liquid such as a medicament. Devices of this type may be provided with a dose counter to indicate the number of doses left in the aerosol dispenser to a user.

U.S. Pat. No. 7,396,341 B2 discloses an inhaler having a dose counter comprising a spindle provided with a slider. The slider has a starting position on the spindle before the device is used for the first time. With each dose the slider is configured to slide along the spindle towards a top end position.

One disadvantage of the design disclosed in U.S. Pat. No. 7,396,341 B2 is that it may be difficult for a user to see the number of doses left in the device.

SUMMARY

A general object of the present disclosure is to provide a dose counting mechanism for an aerosol dispenser which solves or at least mitigates problems of the prior art.

There is hence according to a first aspect of the present disclosure provided a dose counting mechanism for an aerosol dispenser, wherein the dose counting mechanism comprises: a first body structure, a second body structure rotatably attached to the first body structure, an annular dose counter provided with a plurality of teeth along its perimeter, the dose counter being arranged coaxially with the first body structure and the second body structure, each of the first body structure and the second body structure being rotatable relative to the dose counter, a rotatable actuator configured to mesh with the teeth of the dose counter, the actuator being configured to follow the perimeter of the dose counter when the second body structure is rotated relative to the first body structure, and a rotator configured to rotate concurrently with one of the first body structure and the second body structure, the rotator being configured to engage with the actuator when rotation of the first body structure relative to the second body structure is initiated, causing the actuator to rotate about its central axis thereby rotating the dose counter in a first direction.

Since the entire perimeter of the dose counter may be provided with a remaining dose scale, the indication of the number of doses still available may be made more precise than on an axial straight scale, which would typically be much shorter. This enables for a user to better understand how many doses are still available.

One embodiment comprises a ratchet mechanism configured to prevent the dose counter to rotate in a second direction opposite to the first direction. The dose counter may hence be prevented from moving in the second direction or "backwards counting" direction. An aerosol dispenser may typically have a complex mechanical design with a plurality of moving parts close to each other. The ratchet mechanism prevents that any moving part close to the dose counter would engage with the dose counter and cause the dose counter to rotate in the backwards counting direction.

According to one embodiment the dose counter has an inner perimeter surface provided with ratchet teeth forming part of the ratchet mechanism.

According to one embodiment the ratchet mechanism comprises a ratchet arm provided on the second body structure and configured to engage with the ratchet teeth.

According to one embodiment the rotator is a tooth.

According to one embodiment the rotator forms part of the first body structure.

According to one embodiment the actuator is a cogwheel.

According to one embodiment the rotator is arranged adjacent to the dose counter in a radial direction, wherein the actuator is configured to engage with the rotator and with the teeth of the dose counter simultaneously.

According to one embodiment the actuator is provided on the second body structure.

According to one embodiment the dose counter is provided with a remaining dose scale along its external perimeter.

The entire perimeter of the dose counter may form the remaining dose scale.

According to one embodiment the dose counter has an axial tab, the tab being axially aligned with an empty dose indication of the remaining dose scale.

One embodiment comprises a movable activation member configured to be moved axially relative to a central axis of one of the first body structure and the second body structure from a non-triggering position to a triggering position, wherein the activation member is provided with a dose display indicating a remaining dose on the remaining dose scale, wherein the tab is configured to prevent axial movement of the activation member from the non-triggering position to the triggering position when the dose counter is positioned so that the dose display indicates that the remaining dose is the empty dose indication.

A user may hence become aware of that no further doses are available in the aerosol dispenser.

According to one embodiment the dose display is a dose indicator window configured to display the remaining dose.

According to one embodiment the dose counter is arranged radially inside the first body structure.

There is according to a second aspect of the present disclosure provided an aerosol dispenser comprising a dose counting mechanism according to the first aspect. The aerosol dispenser may for example be an inhaler or an eye dispenser.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc.", unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

Figure 1:
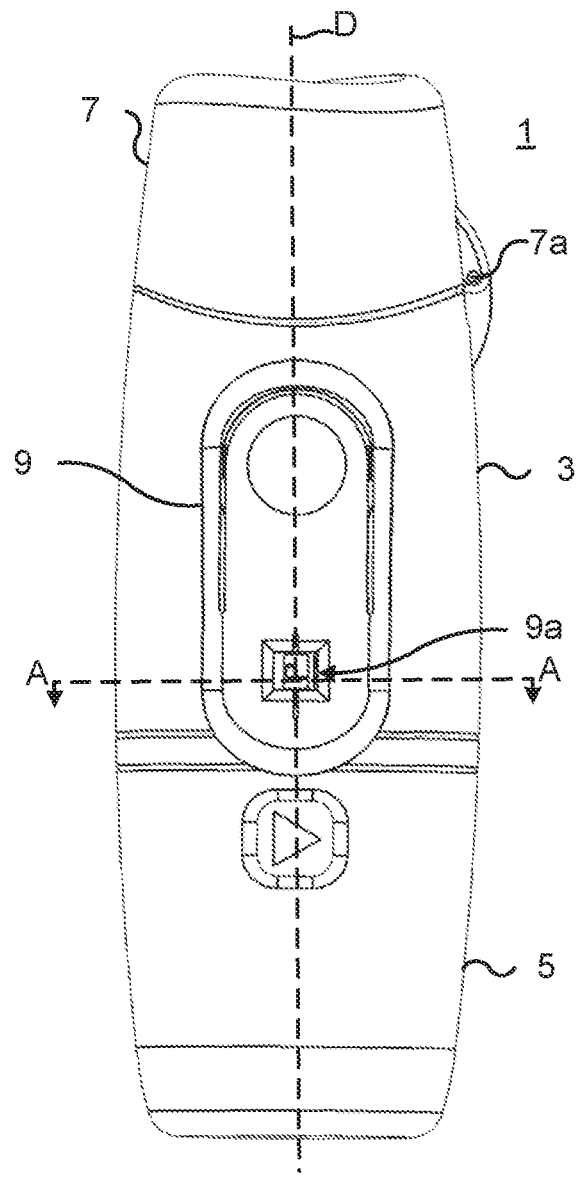
FIG. 1 shows a side view of an example of an aerosol dispenser.

FIG. 1 shows a perspective view of an example of an aerosol dispenser 1, such as an inhaler or an eye dispenser. The aerosol dispenser 1 comprises a first body structure 3 and a housing member 5. The first body structure 3 forms part of an external housing of the aerosol dispenser 1. The housing member 5 also forms part of the external housing of the aerosol dispenser 1.

In the example in FIG. 1, the first body structure 3 and the housing member 5 have an elongated shape and are coaxially arranged. The central axis D of the first body structure 3 and the housing member 5 coincide and form the central axis of the aerosol dispenser 1.

The exemplified aerosol dispenser 1 furthermore comprises an aerosol dispensing end cap 7 attached to the first body structure 3. The aerosol dispensing end cap 7 forms an aerosol dispensing end of the aerosol dispenser 1. The aerosol dispensing end cap 7 is pivotally attached to the first body structure 3. The aerosol dispensing end cap 7 is configured to be pivoted about a pivot axis 7a to open the aerosol dispenser 1 for a dispensing operation.

In the example shown in FIG. 1, the housing member 5 forms a distal end of the aerosol dispenser 1 and the aerosol dispensing end cap 7 forms a proximal end of the aerosol dispenser 1. The first body structure 3 is arranged axially between the housing member 5 and the aerosol dispensing end cap 7.

The first body structure 3 is configured to be rotatably attached to the housing member 5. The aerosol dispenser 1 is configured to be activated by rotation of the housing member 5 relative to the first body structure 3. This rotation may for example be about 180 degrees. Thus, every time that the aerosol dispenser 1 is activated for a dispensing operation the housing member 5 is rotated a predetermined amount such as 180 degrees relative to the first body structure 3.

The aerosol dispenser 1 furthermore comprises an activation member 9 configured to trigger the aerosol dispensing operation when the aerosol dispenser 1 has been activated. The activation member 9 may for example be a push/slide button. The activation member 9 is configured to be arranged in an opening in the first body structure 3. The activation member 9 is configured to slide axially relative to the first body structure 3 between a proximal non-triggering position and a distal triggering position. The activation member 9 can be further received by the first body structure 3 in the triggering position. The activation member 9 is hence radially displaceable in the triggering position, and such radial displacement may be provided by radially pushing the activation member 9. By pushing the activation member 9 in the triggering position a dispensing operation is triggered. The activation member 9 is prevented from such radial displacement in the non-triggering position. Triggering of a dispensing operation is hence prevented.

The exemplified activation member 9 has a dose display 9a indicating the remaining number of doses. The dose display 9a may for example be a dose window.

Figure 2:
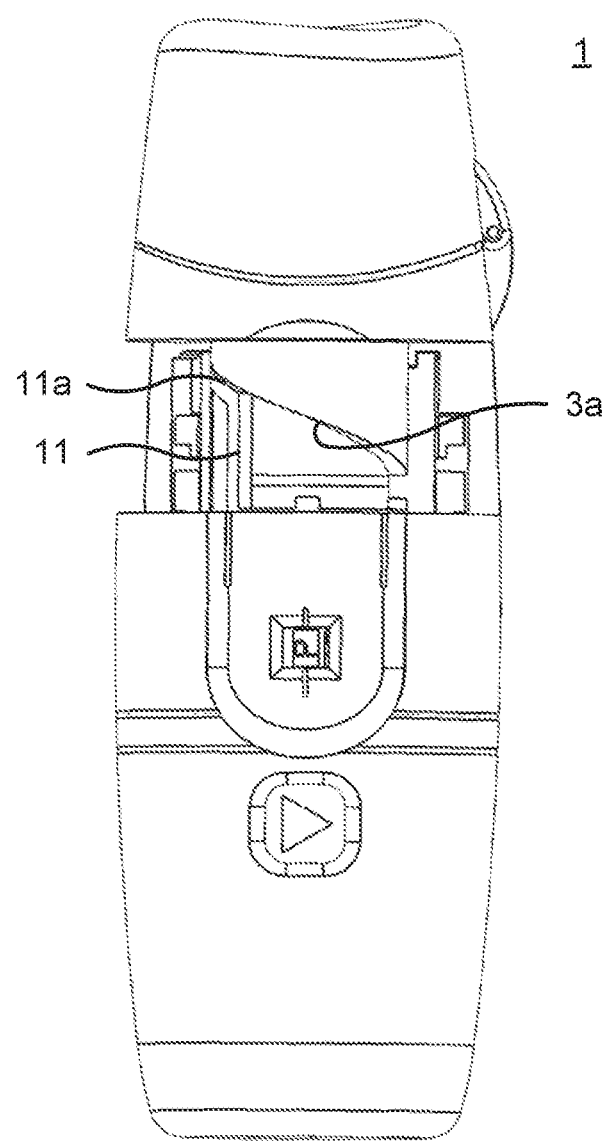
FIG. 2 is a side view of the aerosol dispenser in FIG. 1 with a cut-out portion to expose the interior of the aerosol dispenser.
Figure 3:
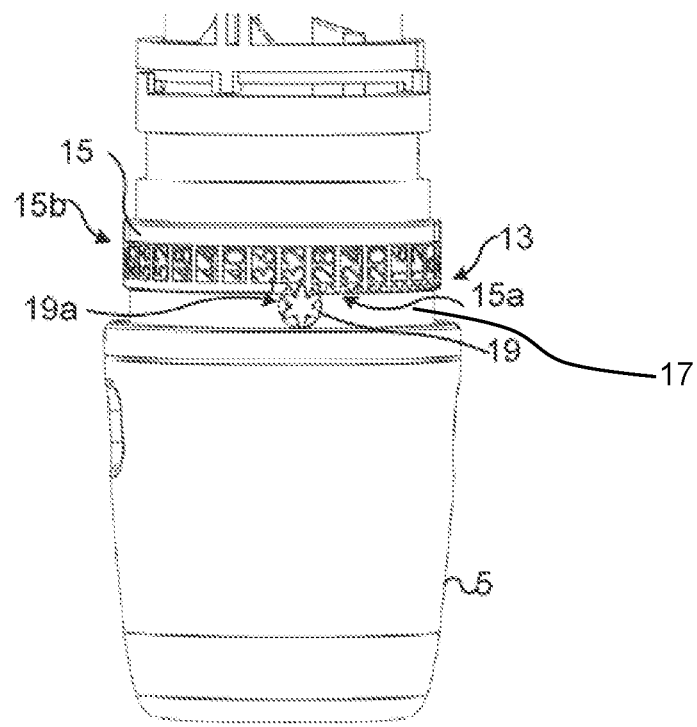
FIG. 3 shows the aerosol dispenser in FIG. 1 with a first body structure removed to expose part of the interior of the aerosol dispenser.
Figure 4:
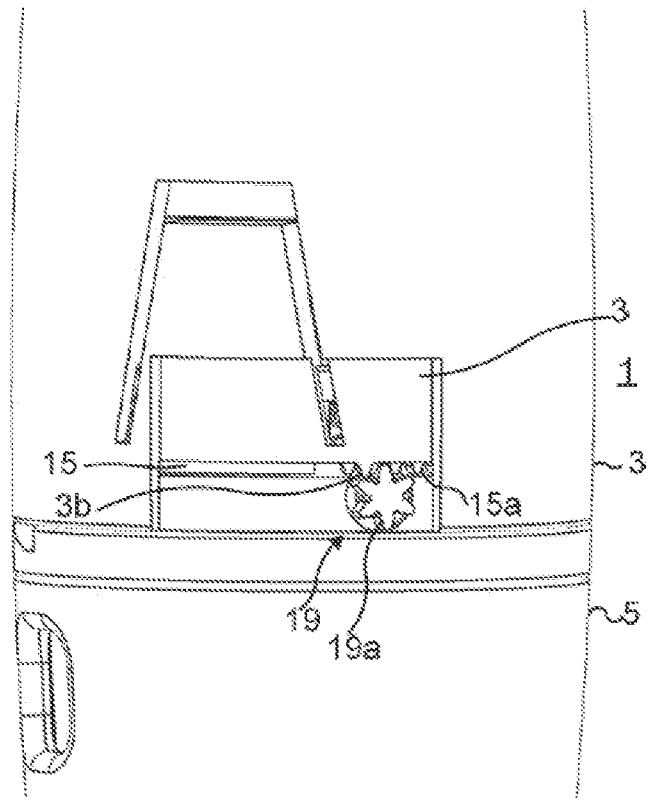
FIG. 4 shows a close-up view of the aerosol dispenser in FIG. 1 having been rotated about it central axis and with a cut-out portion to expose internal components.

FIG. 2 shows the aerosol dispenser 1 with part of the first body structure 3 and the activation member 9 cut away to expose the interior of the aerosol dispenser 1. The aerosol dispenser 1 comprises an axially movable pump sleeve 11 configured to receive and engage with a cartridge. The pump sleeve 11 is configured to be rotationally locked relative to the housing member 5. The pump sleeve 11 is configured to be axially moveable relative to the housing member 5.

The pump sleeve 11 is configured to cooperate with the first body structure 3 such that rotation of the first body structure 3 relative to the housing member 5 causes axial displacement of the pump sleeve relative to the first body structure 3 and relative to the housing member 5. According to the example in FIG. 2, the translation of rotational motion of the first body structure 3 to a linear motion of the sleeve member 11 is obtained by cooperating cam surfaces. Hereto, the first body structure 3 has a first cam surface 3a and the pump sleeve 11 has a second cam surface 11a configured to cooperate with the first cam surface 3a, to translate rotational motion of the first body structure 3 to linear motion of the pump sleeve 11.

The pump sleeve 11 is configured to be biased towards the proximal end of the aerosol dispenser 1. The pump sleeve 11 is configured to be biased such that the second cam surface 11a bears against the first cam surface 3a. The pump sleeve 11 has an elongated needle holding structure provided with a needle (not shown). The needle holding structure extends in the axial direction in the proximal direction towards a spray nozzle assembly of the aerosol dispenser 1. The needle is attached to the pump sleeve 11 inside the needle holding structure and configured to extend axially in the distal direction into the cartridge. When the pump sleeve 11 is moved axially towards the distal end of the aerosol dispenser 1 due to the above-described rotating operation, the volume of a cavity between the needle holding structure and the spray nozzle assembly is increased. An under-pressure with respect to the pressure in the cartridge, which is in fluid communication with the cavity via the needle, is thereby created in the cavity. Liquid from the cartridge is therefore pumped into the cavity. The cavity is thereby filled with a dose to be dispensed. The pump sleeve 11 is maintained in this axial position until the activation member 9 is actuated. The activation member 9 is configured to release the pump sleeve 11 when the activation member 9 is actuated, i.e. pushed in the triggering position. In particular, actuation of the activation member 9 releases the biased pump sleeve 11, causing the pump sleeve 11 to return to its initial position. The size of the liquid-filled cavity is thus reduced as the needle holding structure is moved in the proximal direction, whereby the liquid is pushed out through the spray nozzle assembly, forming an aerosol.

Turning now to FIG. 3, the interior of the aerosol dispenser 1 is shown. The aerosol dispenser 1 comprises a dose counting mechanism 13. The dose counting mechanism 13 is configured to indicate the number of doses left in the aerosol dispenser 1. The dose counting mechanism 13 comprises a second body structure 17 which is an inner sleeve arranged inside the housing member 5. The second body structure 17 is configured to be rotationally fixed relative to the housing member 5. The second body structure 17 is configured to engage with the housing member 5 to prevent relative rotation between the second body structure 17 and the housing member 5. The second body structure 17 extends longitudinally from the housing member 5 into the first body structure 3. The second body structure 17 is arranged concentrically with the first body structure 3 and with the housing member 5. The second body structure 17 is hence contained in the housing member 5 and in the first body structure 5.

The dose counting mechanism 13 comprises an annular dose counter 15. The dose counter 15 is arranged around the second body structure 17. In the present example, the dose counter 15 is arranged around the second body structure 17 in a region which extends into the first body structure 3. The dose counter 15 is arranged concentrically with the second body structure 17. Alternatively, the dose counter could be arranged around the second body structure in a region which is within the housing member 5 with the teeth pointing in the proximal direction towards the actuator, instead of pointing in the distal direction.

The dose counter 15 is configured to be rotatably arranged relative to the second body structure 17. The dose counter 15 is hence able to rotate relative to the second body structure 17. The dose counter 15 is configured to be rotatably arranged relative to the first body structure 3. The dose counter 15 is hence able to rotate relative to the first body structure 3. The dose counter 15 is provided with a plurality of teeth 15*a* arranged one after the other in the circumferential direction along the perimeter of the dose counter 15. In the example shown in FIG. 3, the teeth 15*a* are pointing axially towards the distal end of the aerosol dispenser 1.

The dose counter 15 is provided with a remaining dose scale 15*b* along its external perimeter. The remaining dose scale 15*b* provides an indication of the remaining number of doses left in the aerosol dispenser 1. The remaining dose scale 15*b* may for example comprise printing or etching of the number of doses left as shown in FIG. 3. The activation member 9 is configured to display the remaining dose scale 15*b* through the dose display 9*a*, which in the present example is a dose window. The activation member 9 may in particular be configured to display the currently remaining number of doses through the dose display 9*a*, as for example can be seen in FIG. 1 where the letter "P" is shown through the dose display 9*a*. "P" stands for "primer" which is a primer dose that may be dispensed before the first dose used by the user is dispensed.

The dose counting mechanism 13 furthermore comprises an actuator 19. The actuator 19 is rotatable. The actuator 19 is configured to be rotatably attached to the second body structure 17. The actuator 19 may be configured to freely rotate relative to the second body structure 17 about an axis which is perpendicular to the central axis D. The exemplified actuator 19 extends radially outwards from the second body structure 17. The actuator 19 may have a radially extending axle and the actuator 19 may be attached to the second body structure 17 by means of the axle, which may extend into or through the wall of the second body structure 17. The actuator 19 is configured to at least partly radially align with the dose counter 15. In particular, the actuator 19 is configured to engage with the teeth 15*a* of the dose counter 15. The actuator 19 may for example be a cogwheel. The actuator 19 in the form of a cogwheel is provided with cogs 19 configured mesh with the teeth 15*a* of the dose counter 15. Rotation of the dose counter 15 hence causes rotation of the actuator 19. Rotation of the actuator 19 may also cause rotation of the dose counter 15, as will be explained in more detail in the following.

FIG. 4 shows the aerosol dispenser 1 with a portion of the outer wall of the first body structure 3 cut out to expose further components of the dose counting mechanism 13. The dose counting mechanism 13 furthermore comprises a rotator 3*b*. The rotator 3*b* is configured to cause movement of the actuator 19. The rotator 3*b* is configured to rotate the actuator 19.

The exemplified rotator 3*b* is fixed relative to the first body structure 3. The rotator 3*b* may form part of the first body structure 3. For example the first body structure 3 may have an inner surface flange or cut-out and the rotator 3*b* may extend from the flange or radial surface of the cut-out towards the actuator 19. The rotator 3*b* may be a protrusion or tooth which points axially towards the distal end of the aerosol dispenser 1. The rotator 3*b* may for example comprise a single protrusion or tooth or more than one protrusion or tooth.

The rotator 3*b* is configured to engage with the actuator 19. The rotator 3*b* is configured to be arranged radially adjacent to the dose counter 15. The rotator 3*b* may be arranged radially outside of the dose counter 15. The actuator 19 may have a thickness or extension in the radial direction such that it is able to engage with the rotator 3*b* and with the teeth 15*b* of the dose counter 15 simultaneously. Thus, when the housing member 5 is being rotated relative to the first body structure 3, the rotator 3*b* engages with the actuator 19, causing the actuator 19 to rotate an amount corresponding to movement of one tooth 19*a* of the actuator 19 from one side of the rotator 3*b* to the other side thereof, i.e. from one flank to the other flank of the rotator 3*b*. The rotator 3*b* is hence configured to drive the actuator 19. Since the actuator 19 simultaneously engages with the teeth 15*a* of the dose counter 15, the dose counter 15 is rotated about the central axis of the aerosol dispenser 1. This rotation may correspond to the pitch of the teeth 15*a*, i.e. the tooth to tooth or flank to flank distance. Since the dose counter 15 is provided with the remaining dose scale, the remaining number of doses as shown in the dose display 9*a* of the activation member 9 will be updated, in particular counted down. In case not all of the doses are displayed on the remaining dose scale 15*b*, but only for example every $N^{th}$ dose, then the number of teeth 15a between two visual indications on the remaining dose scale 15b may for example be N and so the dose counter 15 will be rotated such that the activation member 9 displays dose n+N instead of dose n when the aerosol dispenser 1 has been activated and triggered N times.

Once the actuator 19 has meshed with and passed the rotator 3b the actuator 19 is rotated freely by it meshing with the teeth 15a of the dose counter 15, as the second body structure 17 is being further rotated relative to the first body structure 3. No additional rotation of the dose counter 15 is hence provided, since in this case the dose counter 15 drives the actuator 19.

Figure 5:
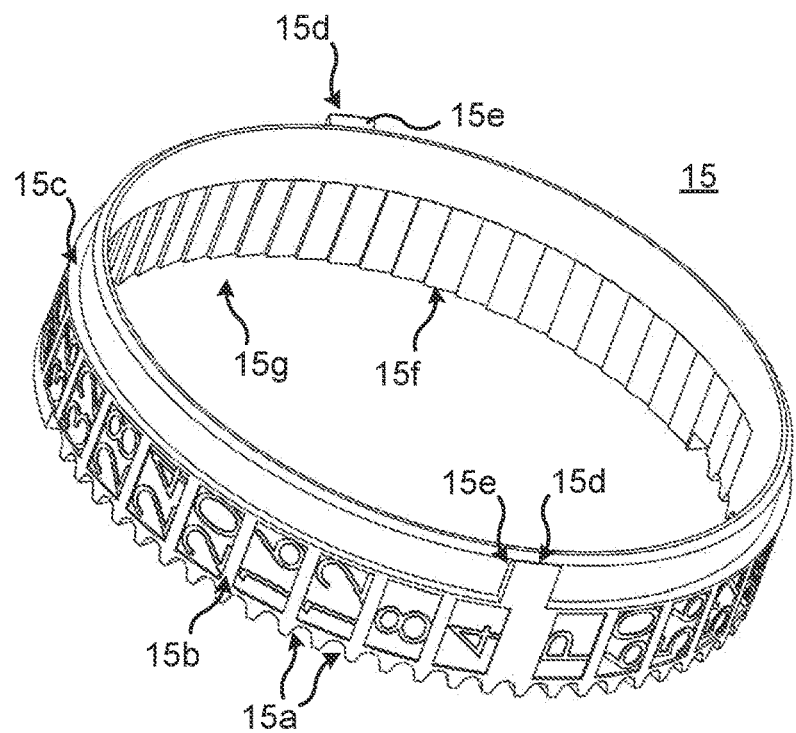
FIG. 5 is a perspective view of an example of a dose counter.

FIG. 5 shows a perspective view of the dose counter 15. The exemplified dose counter 15 comprises a flange surface 15c. The dose counter 15 comprises one or more an axial tab(s) 15d extending axially from the flange surface 15c. In the present example, the axial tab 15d extends axially from the flange surface 15c in the proximal direction. The axial tab 15d may have a chamfered end face 15e in a longitudinal section of the aerosol dispenser 1. The tab 15d is preferably arranged axially aligned with the empty dose indication of the remaining dose scale 15b.

According to the present example, the teeth 15a are provided only along about 180 degrees of the perimeter of the dose counter 15. Alternatively, the teeth could extend for example along the entire perimeter.

The dose counter 15 may be provided with a plurality of ratchet teeth 15f. The dose counter 15 has an inner perimeter surface 15g and the inner perimeter surface 15g may be provided with the ratchet teeth 15f. The ratchet teeth 15f are configured to enable rotation of the dose counter 15 in a first direction which is the dose countdown direction. The ratchet teeth 15f are configured to prevent rotation of the dose counter 15 in a second direction opposite to the first direction. It can thereby be ensured that the doses indicated by the dose display 9a are the actual number of doses remaining in the aerosol dispenser 1.

Figure 6:
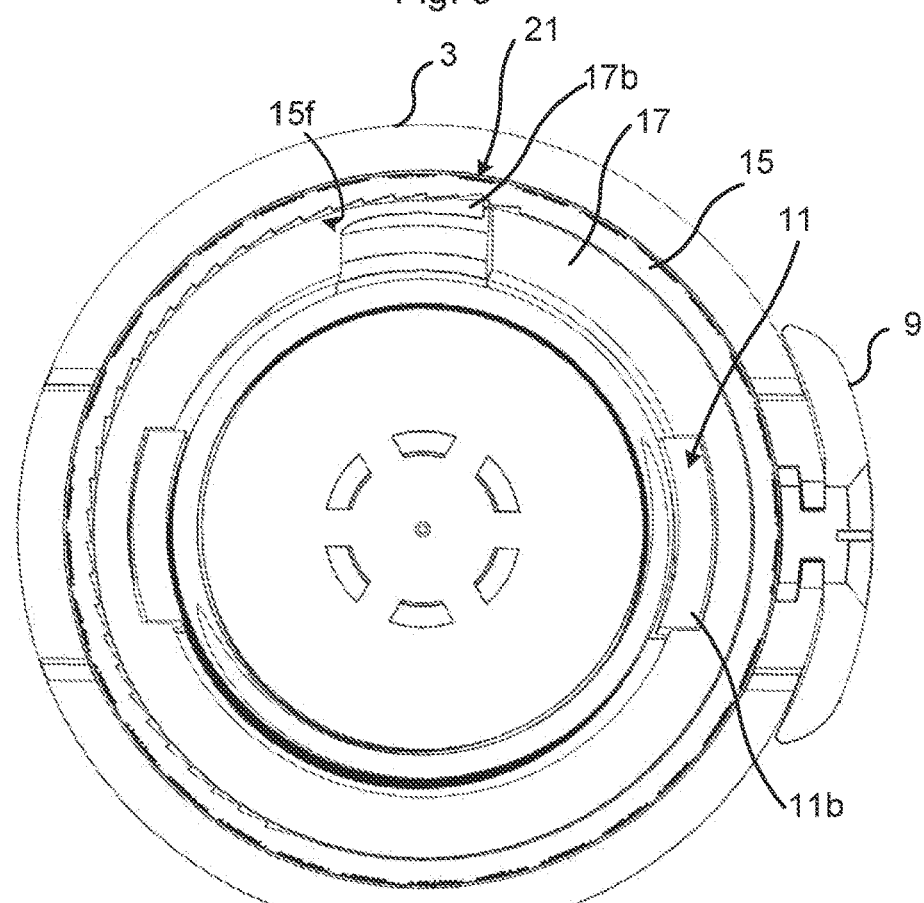
FIG. 6 is a cross-section of the aerosol dispenser along lines A-A.

FIG. 6 is a cross-section along lines A-A in FIG. 1. The rotational locking between the second body structure 17 and the pump sleeve 11 can be seen. In this example, the pump sleeve 11 has axial ribs 11b extending radially outwards and the second body structure 17 has corresponding recesses 17a configured to receive a respective one of the axial ribs 11b. This configuration allows relative axial displacement between the pump sleeve 11 and the second body structure 17.

The second body structure 17 comprises a ratchet arm 17b configured to cooperate with the ratchet teeth 15f of the dose counter 15. The ratchet arm 17b is radially flexible and extends radially outwards and is configured to engage with the ratchet teeth 15f. The ratchet teeth 15f and the ratchet arm 17b form a ratchet mechanism 21.

Figure 7:
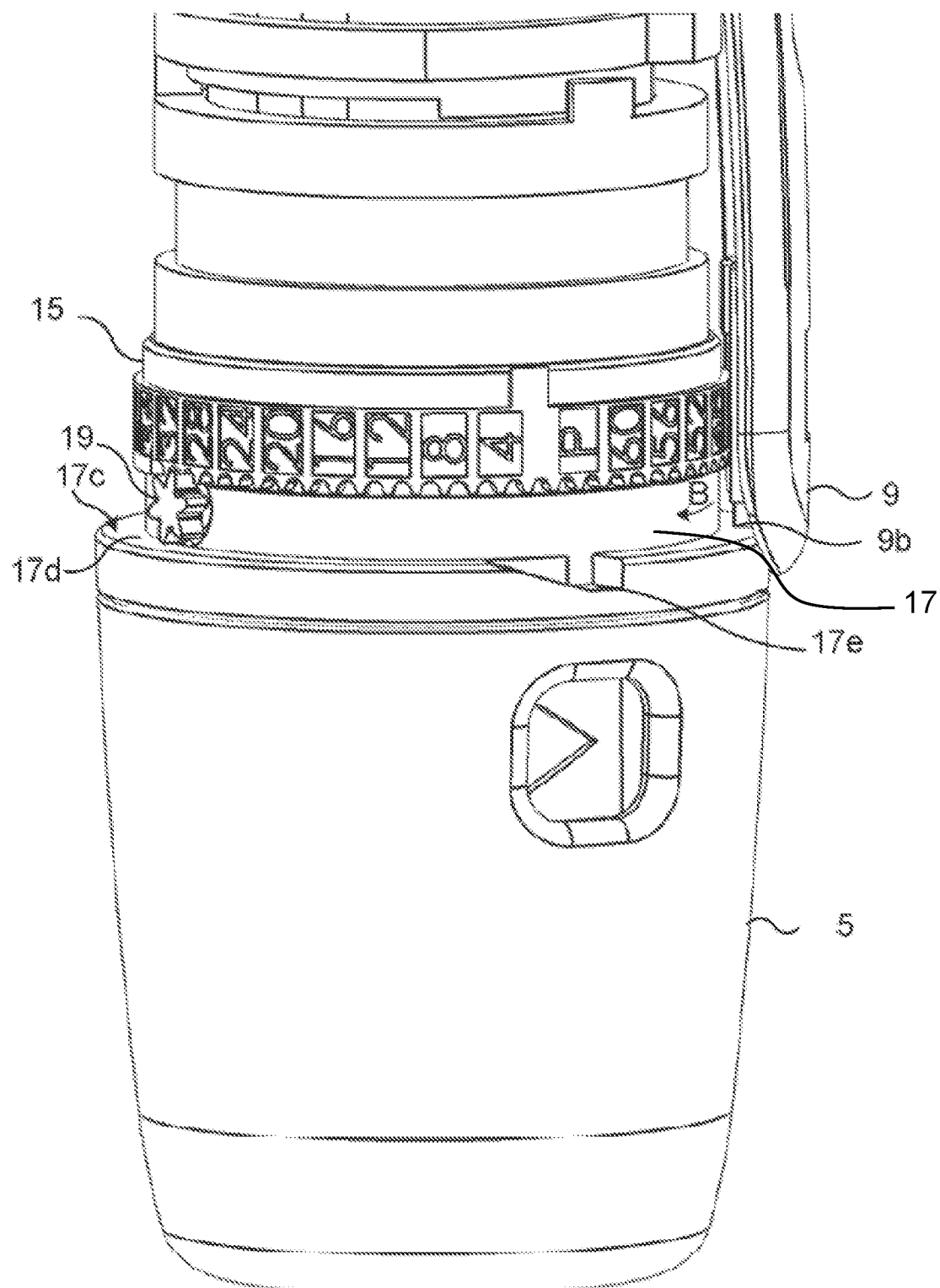
FIG. 7 is a perspective view of the aerosol dispenser in FIG. 1 with the first body structure removed.

FIG. 7 further depicts the operation of the activation member 9. The second body structure 17 comprises a flange structure 17c which defines a radial surface 17d facing the proximal end of the aerosol dispenser 1. The radius of the second body structure 17 hence becomes smaller adjacent to the radial surface, in the proximal direction of the aerosol dispenser 1. The actuator 19 is mounted to the second body structure 17 in this region with a smaller radius. The dose counter is mounted around this region of the second body structure 17, proximally from the actuator 19. The flange structure 17c is provided with an axial recess 17e. Hereto, the radial surface 17d is provided with the axial recess 17e. The axial recess 17e has a stepped axial depth configuration at one end thereof in the peripheral direction and a gradually smoothly increasing axial depth at the opposite end. The activation member 9 has a guide heel 9b. The activation member 9 is configured to bear against the radial surface 17d by means of the guide heel 9b. Thus, as the housing member 5 and thus the second body structure 17 is being rotated relative to the first body structure 3, the activation member 9 will slide along the radial surface 17d. When the guide heel 9b rests against the radial surface 17d outside of the axial recess 17e, the activation member 9 is in the non-triggering position. The activation member 9 may be biased towards the triggering position. However, when the activation member 9 moves in the direction B and the guide heel 9b eventually aligns with the axial recess 17e, the activation member 9 will be able to be moved in the distal direction from the non-triggering position to the triggering position in which the guide heel 9b rests in the axial recess 17e. Triggering of the aerosol dispenser 1 is thereby enabled. In a subsequent activation or loading operation, the activation member 9 is able to move out from the axial recess 17e into the non-triggering position until the first body structure 3 has been rotated for example about 180 degrees, where an additional axial recess of the same type as axial recess 17e may be provided, allowing the activation member 9 to move to the triggering position.

Figure 8A:
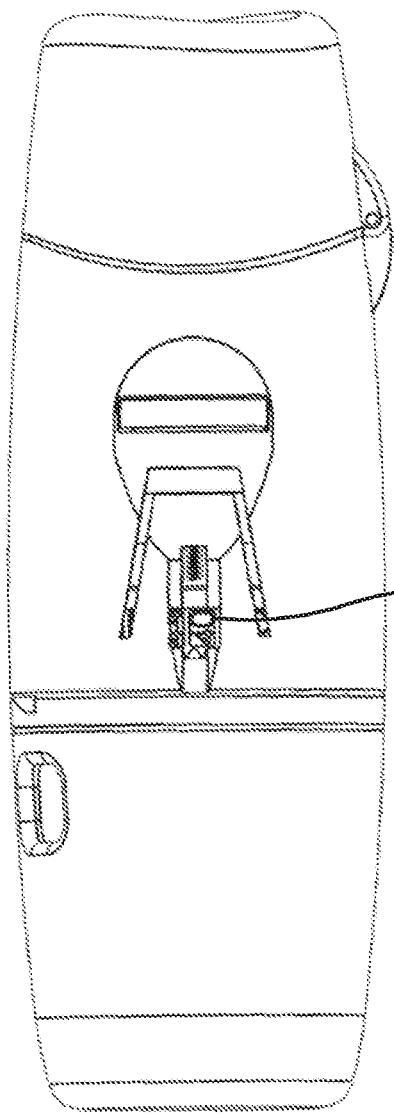
FIG. 8a depicts the aerosol dispenser in a state of operation.
Figure 8B:
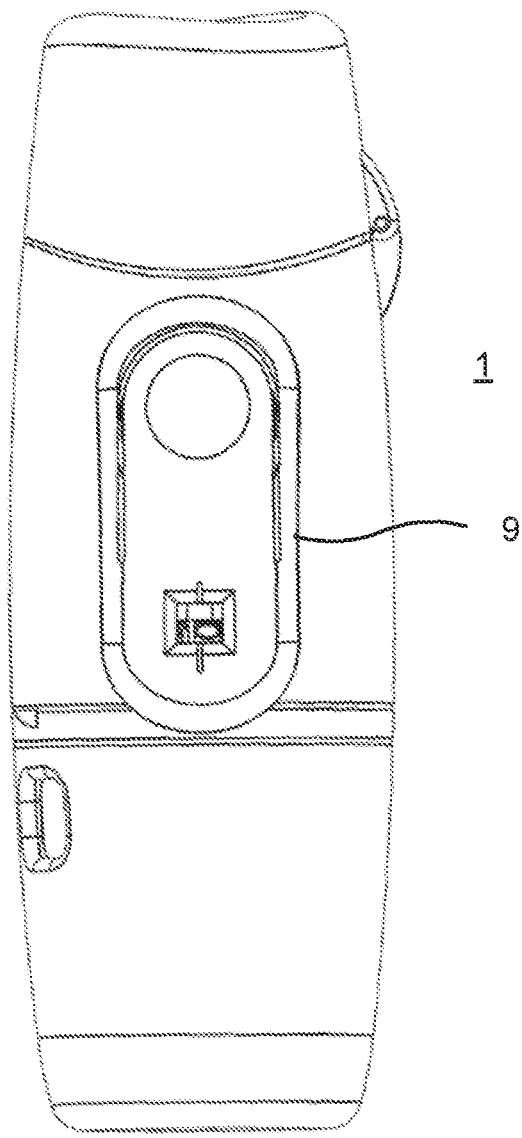
FIG. 8b depicts the aerosol dispenser in a state of operation.
Figure 8C:
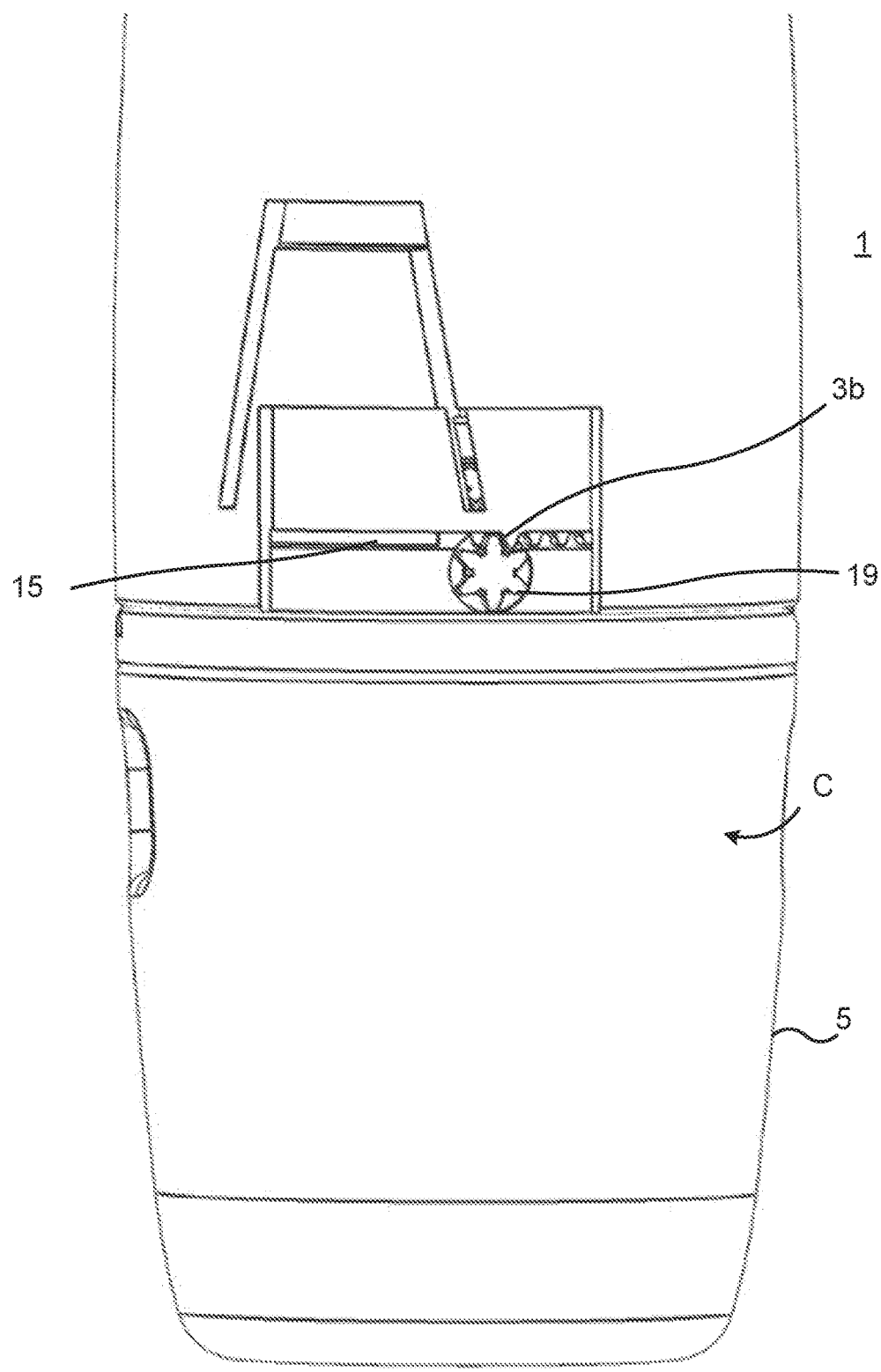
FIG. 8c depicts the aerosol dispenser in a state of operation.

The operation of the aerosol dispenser 1 and in particular of the locking mechanism will now be described in more detail with reference to FIGS. 8a-10. FIG. 8a shows the aerosol dispenser 1 without the activation member 9, which in this case would be in the non-triggering position. The remaining dose scale 15b shows that about 40 doses are still available. In FIG. 8b the activation member 9 is also shown. In the non-triggering position, the remaining dose scale 15b is not fully visible in the dose display 9a. FIG. 8c shows the actuator 19 prior to meshing with the rotator 3b. The housing member 5 is rotated in direction C which causes cooperation between the tooth 19a of the actuator 19 and the rotator 3b. The rotator 3b drives the actuator 19 which in turn drives the dose counter 15.

Figure 9A:
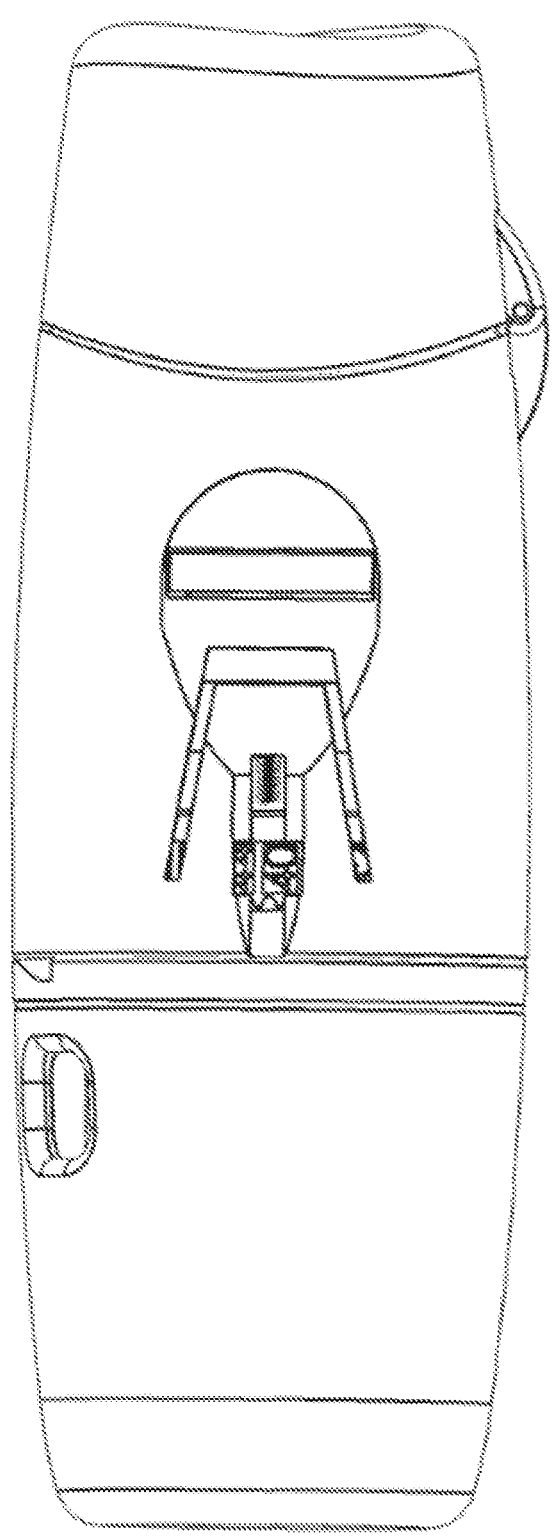
FIG. 9a depicts the aerosol dispenser in a state of operation.
Figure 9B:
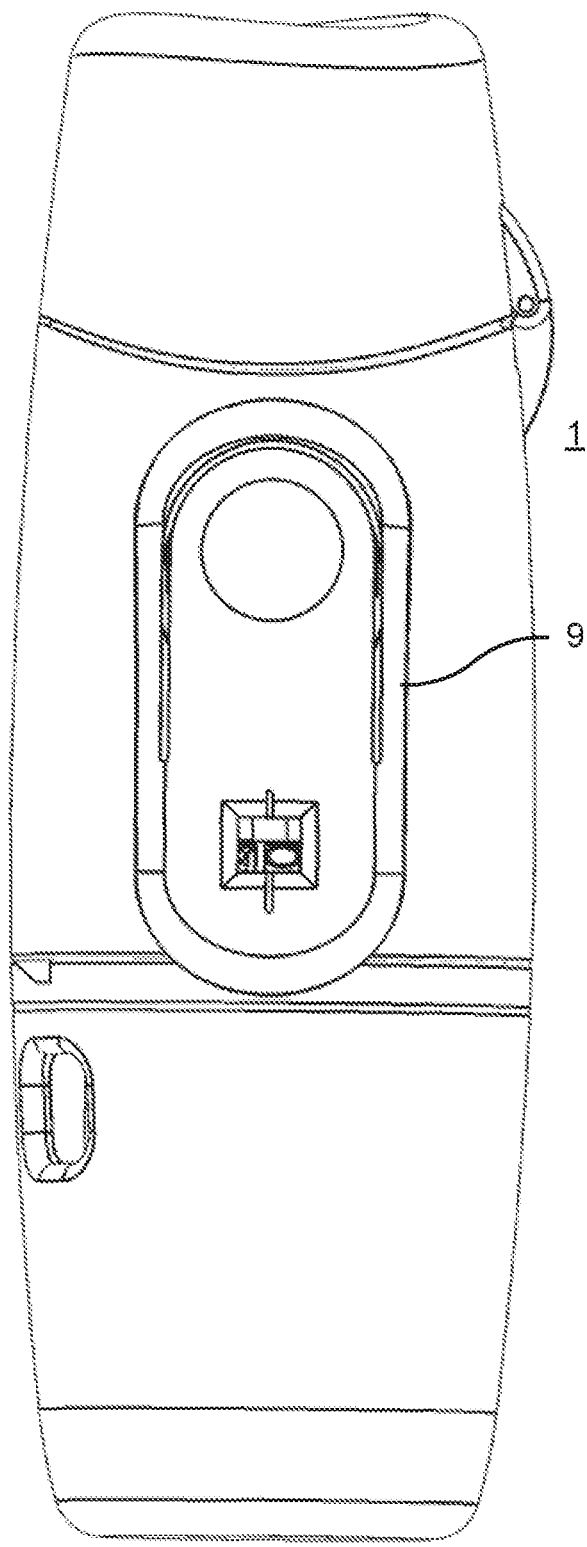
FIG. 9b depicts the aerosol dispenser in a state of operation.
Figure 9C:
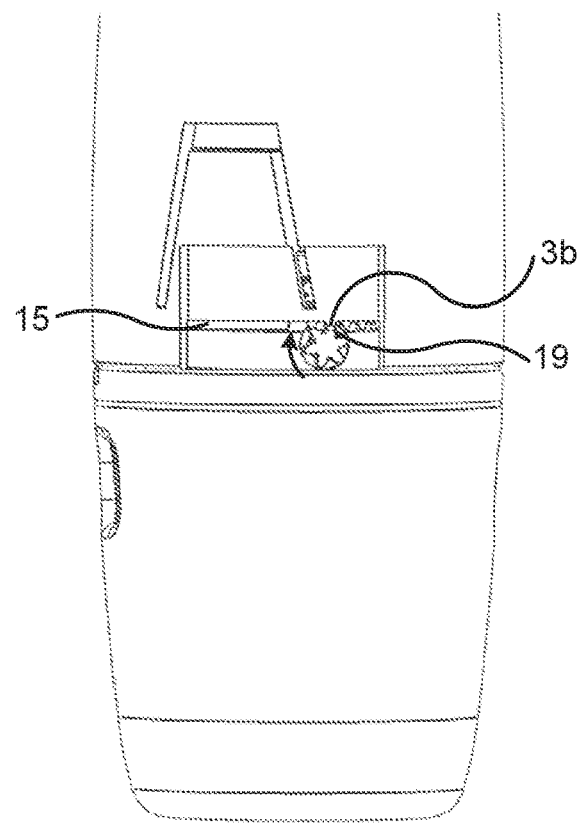
FIG. 9c depicts the aerosol dispenser in a state of operation.

In FIG. 9a the activation member 9 is removed. The remaining dose scale 15b has been rotated one increment by cooperation between the actuator 19 and the teeth 15a of the dose counter 15 and one dose has thus been dispensed. FIG. 9b shows this situation with the activation member 9 visible. In FIG. 9c it can be seen that the actuator 19 has been rotated with respect to its position in FIG. 8c such that the tooth 19b has passed the rotator 3b, i.e. the tooth 19b which in FIG. 8c bore against the left flank of the rotator 3b in the figure now bears against the right flank of the rotator 3b. The dose counter 15 has thereby rotated one increment.

Figure 10:
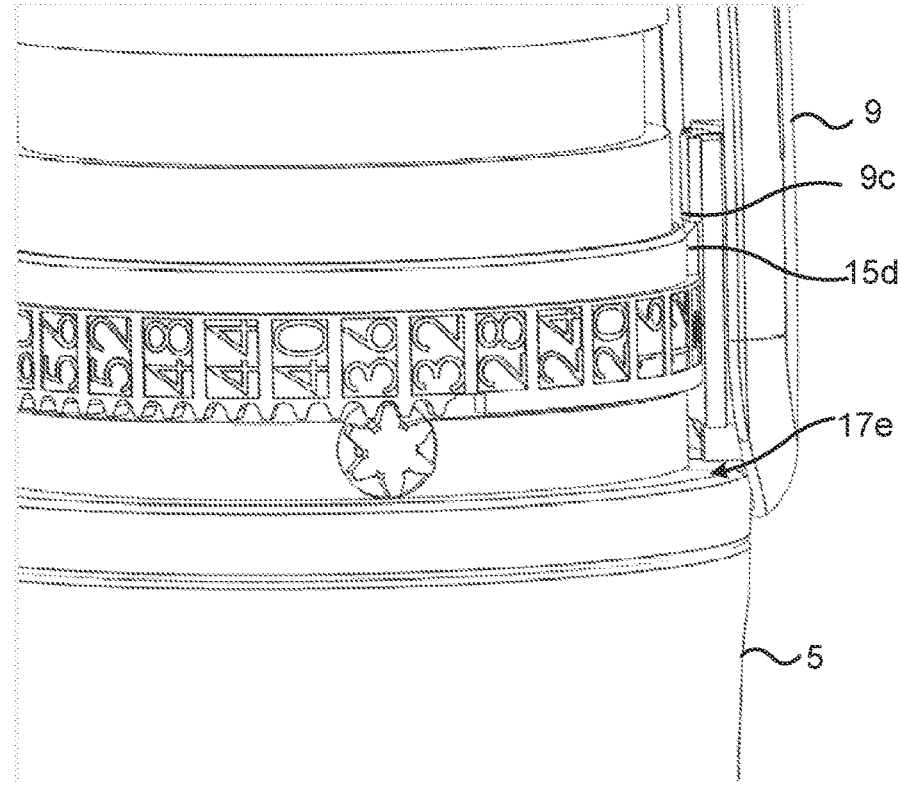
FIG. 10 depicts the aerosol dispenser in a state of operation.

FIG. 10 shows a situation in which the final dose has been dispensed from the aerosol dispenser 1. The aerosol dispenser 1 has been loaded by rotation of the housing member 5 relative to the first body structure 3. The activation member 9 has thus been aligned with the axial recess 17e. The activation member 9 has a blocking heel 9c extending radially inwards and configured to align and bear against the tab 15d of the dose counter 15 when the dose counter 15 has been rotated to display that that there are no more doses available, i.e. when remaining dose is the empty dose indication. The blocking heel 9c is in this case arranged proximally relative to the tab 15d. The activation member 9 is thereby prevented from moving from the non-triggering position to the triggering position. A user will hence become aware of that the no further doses are available in the aerosol dispenser 1.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A dose counting mechanism for an aerosol dispenser, wherein the dose counting mechanism comprises: a first body structure, a second body structure rotatably attached to the first body structure, an annular dose counter provided with a plurality of teeth along its perimeter, the dose counter being arranged coaxially with the first body structure and the second body structure, the dose counter being rotatable relative to the first body structure and the second body structure, a rotatable actuator configured to mesh with the teeth of the dose counter, the actuator being configured to follow the perimeter of the dose counter when the second body structure is rotated to the first body structure, a rotator configured to rotate concurrently with one of the first body structure and the second body structure, the rotator being configured to engage with the actuator when rotation of the first body structure relative to the second body structure is initiated, causing the actuator to rotate about its central axis thereby rotating the dose counter in a first direction, a remaining dose scale along the perimeter, an axial tab, wherein the tab is axially aligned with an empty dose indication of the remaining dose scale; and a movable activation member configured to be moved axially relative to a central axis of one of the first body structure and the second body structure, from a non-triggering position to a triggering position, wherein the activation member is provided with a dose display indicating a remaining dose on the remaining dose scale, wherein the tab is configured to prevent axial movement of the activation member from the non-triggering position to the triggering position when the dose counter is positioned so that the dose display indicates that the remaining dose is the empty dose indication.

2. The dose counting mechanism as claimed in claim 1, comprising a ratchet mechanism configured to prevent the dose counter to rotate in a second direction opposite to the first direction.

3. The dose counting mechanism as claimed in claim 2, wherein the dose counter has an inner perimeter surface provided with ratchet teeth forming part of the ratchet mechanism.

4. The dose counting mechanism as claimed in claim 3, wherein the ratchet mechanism comprises a ratchet arm provided on the second body structure and configured to engage with the ratchet teeth.

5. The dose counting mechanism as claimed in claim 1, wherein the rotator is a tooth.

6. The dose counting mechanism as claimed in claim 1, wherein the rotator forms part of the first body structure.

7. The dose counting mechanism as claimed in claim 1, wherein the actuator is a cogwheel.

8. The dose counting mechanism as claimed in claim 1, wherein the rotator is arranged adjacent to the dose counter in a radial direction, wherein the actuator is configured to engage with the rotator and with the teeth of the dose counter simultaneously.

9. The dose counting mechanism as claimed in claim 1, wherein the actuator is provided on the second body structure.

10. The dose counting mechanism as claimed in claim 1, wherein the dose display is a dose indicator window configured to display the remaining dose.

11. The dose counting mechanism as claimed in claim 1, wherein the dose counter is arranged radially inside the first body structure.

12. An aerosol dispenser comprising a dose counting mechanism as claimed in claim 1.

13. A dose counting mechanism for an aerosol dispenser, wherein the dose counting mechanism comprises: a first body structure, a second body structure rotatably attached to the first body structure, an annular dose counter provided with a plurality of teeth along its perimeter, the dose counter being arranged coaxially with the first body structure and the second body structure, the dose counter being rotatable relative to the first body structure and the second body structure, a rotatable actuator configured to mesh with the teeth of the dose counter, the actuator being configured to follow the perimeter of the dose counter when the second body structure is rotated to the first body structure, a rotator configured to rotate concurrently with one of the first body structure and the second body structure, the rotator being configured to engage with the actuator when rotation of the first body structure relative to the second body structure is initiated, causing the actuator to rotate about its central axis thereby rotating the dose counter in a first direction; a remaining dose scale along the perimeter, an axial tab, wherein the tab is axially aligned with an empty dose indication of the remaining dose scale; and a movable activation member configured to be moved axially relative to a central axis of one of the first body structure and the second body structure, from a non-triggering position to a triggering position, wherein the activation member is provided with a dose display indicating a remaining dose on the remaining dose scale, wherein the tab is configured to prevent axial movement of the activation member from the non-triggering position to the triggering position when the dose counter is positioned so that the dose display indicates that the remaining dose is the empty dose indication; and a ratchet mechanism that prevents the dose counter from rotating in a second direction opposite to the first direction.

14. The dose counting mechanism of claim 13, wherein the dose counter comprises an inner perimeter surface provided with ratchet teeth forming part of the ratchet mechanism.

15. The dose counting mechanism of claim 13, wherein the dose counter is arranged radially inside the first body structure.

16. The dose counting mechanism of claim 15, wherein the rotator is a tooth and the actuator is a cogwheel.

17. The dose counting mechanism as claimed in claim 13, wherein the dose counter is provided with the remaining dose scale along its external perimeter.

* * * * *